US00PP37600P2

(12) United States Plant Patent
Mathey

(10) Patent No.: US PP37,600 P2
(45) Date of Patent: Aug. 18, 2026

(54) ***ILEX* PLANT NAMED 'SMNIGCM'**

(50) Latin Name: *Ilex glabra*
Varietal Denomination: SMNIGCM

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 19/383,649

(22) Filed: Nov. 8, 2025

(51) Int. Cl.
*A01H 5/00* (2018.01)
*A01H 6/00* (2018.01)

(52) U.S. Cl.
USPC ..... Plt./247

(58) Field of Classification Search
USPC ..... Plt./247
CPC ... A01H 5/00; A01H 5/08; A01H 5/12; A01H 6/00
See application file for complete search history.

(56) References Cited

U.S. PATENT DOCUMENTS

PP27,554 P3 * 1/2017 Wood ..... A01H 6/00 Plt./246

* cited by examiner

*Primary Examiner* — June Hwu
(74) *Attorney, Agent, or Firm* — C. Anne Whealy

(57) ABSTRACT

A new and distinct *Ilex* plant named 'SMNIGCM', characterized by its compact and low and uniformly mounding plant habit; freely branching habit; dense and bushy growth habit; glossy dark green-colored leaves; glossy black-colored fruits; good garden performance; and resistance to Holly Leaf Blight and Holly Rust pathogens.

3 Drawing Sheets

Figure 1:
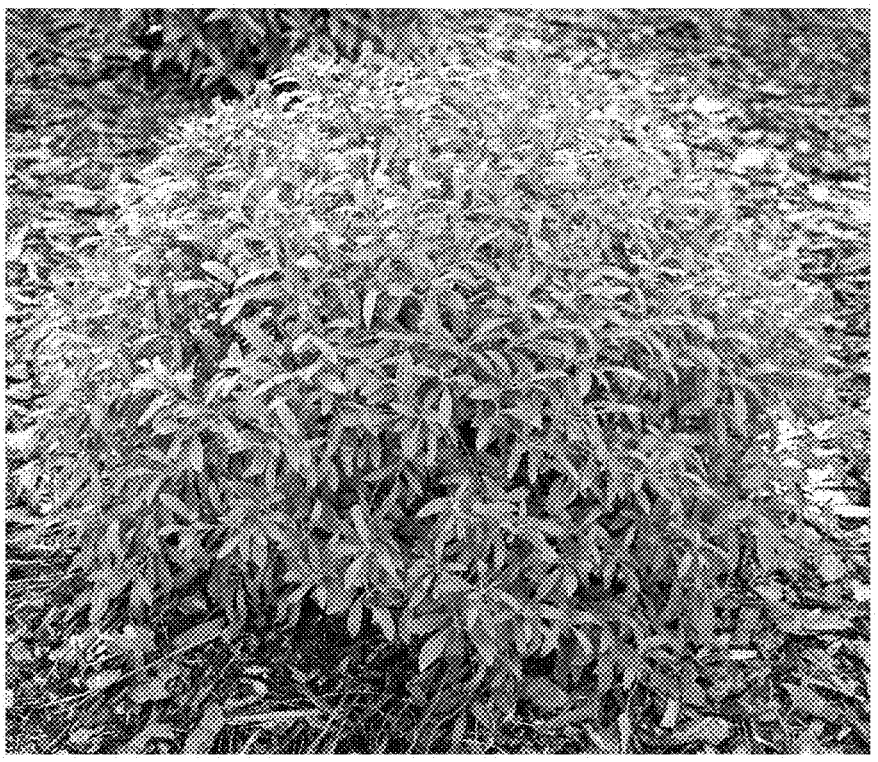

Botanical designation: *Ilex glabra*.
Cultivar denomination: 'SMNIGCM'.

BACKGROUND OF THE INVENTION

The present Invention relates to a new and distinct *Ilex* plant, botanically known as *Ilex glabra*, commonly referred to as Inkberry and hereinafter referred to by the name 'SMNIGCM'.

The new *Ilex* plant is a product of a planned breeding program conducted by the Inventor in Grand Haven, Michigan. The objective of the breeding program was to develop new uniform *Ilex* plants with unique plant habit and form.

The new *Ilex* plant originated from an open-pollination during the summer of 2013 of an unnamed proprietary selection of *Ilex glabra*, not patented, as the female, or seed, parent with an unknown proprietary selection of *Ilex glabra*, as the male, or pollen, parent. The new *Ilex* plant was discovered and selected by the Inventor during the summer of 2019 as a single plant within the progeny of the stated open-pollination in a controlled environment in Grand Haven, Michigan.

Asexual reproduction of the new *Ilex* plant by softwood cuttings in Grand Haven, Michigan since the summer of 2019 has shown that the unique features of the new *Ilex* plant are stable and reproduced true to type in successive generations of asexual reproduction.

SUMMARY OF THE INVENTION

Plants of the new *Ilex* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'SMNIGCM'. These characteristics in combination distinguish 'SMNIGCM' as a new and distinct *Ilex* plant:

1. Compact and low and uniformly mounding plant habit.
2. Freely branching habit; dense and bushy growth habit.
3. Glossy dark green-colored leaves.
4. Glossy black-colored fruits.
5. Good garden performance.
6. Resistant to Holly Leaf Blight and Holly Rust pathogens.

Plants of the new *Ilex* differ primarily from plants of the female parent selection in plant habit as plants of the new *Ilex* are more uniform than plants of the female parent selection.

Plants of the new *Ilex* can be compared to the plants of *Ilex glabra* 'Shamrock', not patented. In side-by-side comparisons, plants of the new *Ilex* differ from plants of 'Shamrock' in the following characteristics:

1. Plants of the new *Ilex* are more compact than plants of 'Shamrock'.
2. Plants of the new *Ilex* are hemispherical in overall shape whereas plants of 'Shamrock' are more spherical in overall shape.
3. Leaves of plants of the new *Ilex* are narrower than leaves of plants of 'Shamrock'.

BRIEF DESCRIPTION OF THE PHOTOGRAPHS

The accompanying colored photographs illustrate the overall appearance of the new *Ilex* plant. The photographs show the colors as true as it is reasonably possible to obtain in colored reproductions of this type. Colors in the photographs may differ slightly from the color values cited in the detailed botanical description which accurately describe the colors of the new *Ilex* plant.

The photograph on the first sheet (FIG. 1) is a side perspective view of a typical vegetative plant of 'SMNIGCM'.

Figure 2:
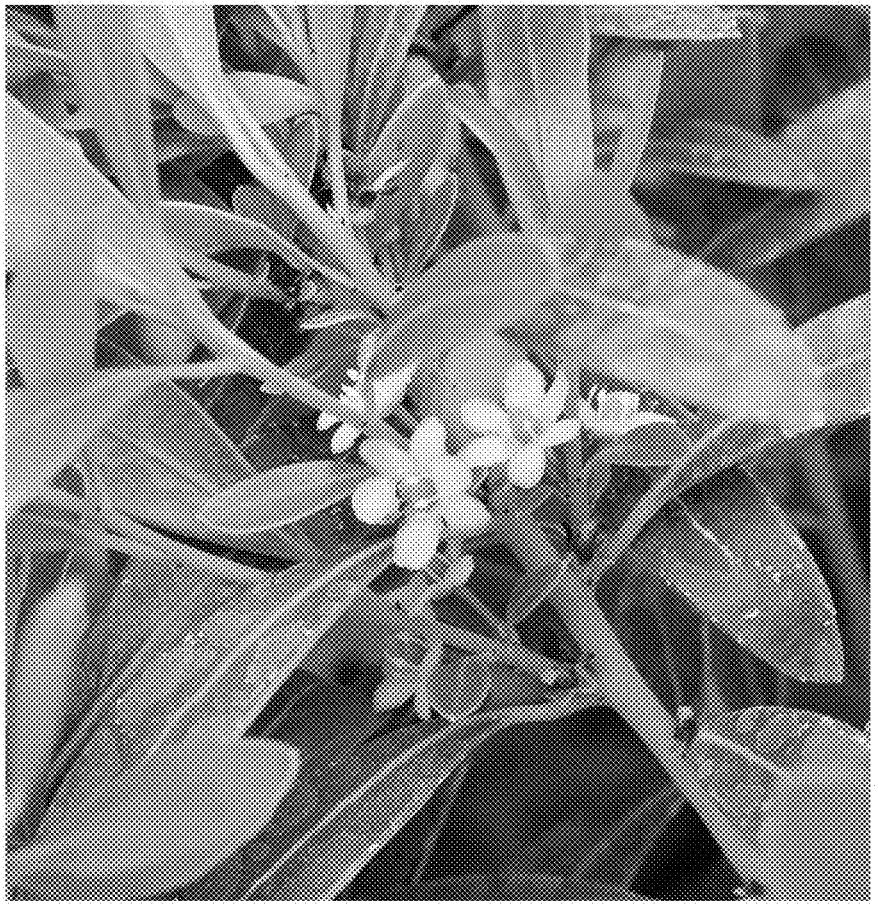

The photograph on the second sheet (FIG. 2) is a close-up view of a typical flowering stem of 'SMNIGCM'.

Figure 3:
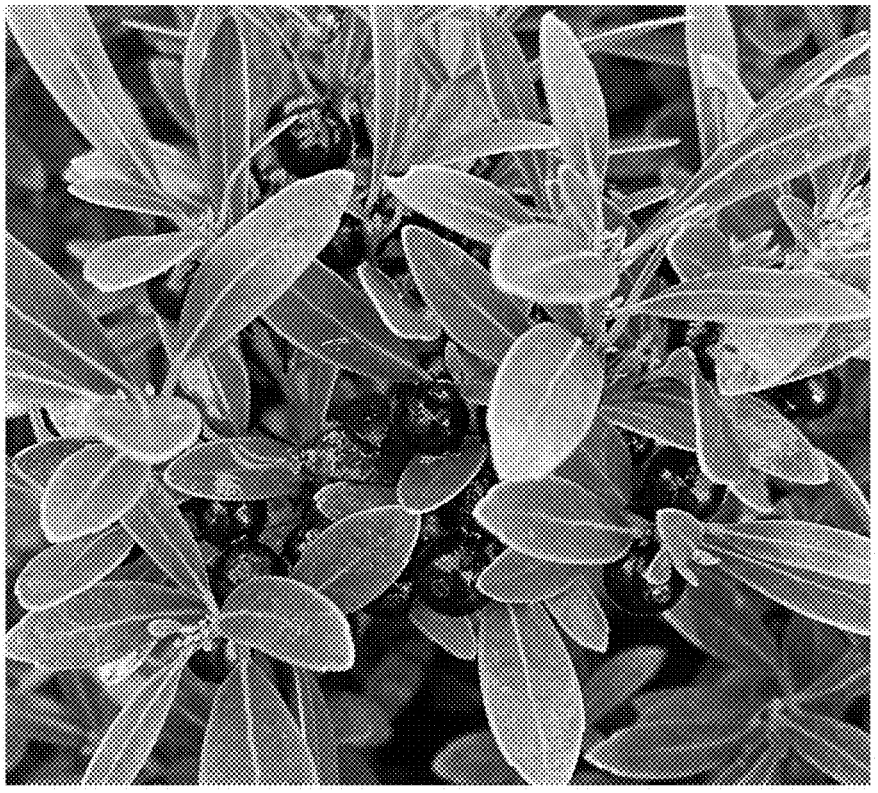

The photograph on the third sheet (FIG. 3) is a close-up view of a typical fruiting plant of 'SMNIGCM'.

Plants used for the aforementioned photographs were grown in an outdoor nursery in Grand Haven, Michigan during late spring and summer and were two years old.

DETAILED BOTANICAL DESCRIPTION

The following observations and measurements describe plants grown during the spring and early summer in three-gallon containers in a polyethylene-covered greenhouse and outdoor nursery in Grand Haven, Michigan and under cultural practices typical of commercial *Ilex* production. During the production of the plants, day temperatures ranged from 18° C. to 27° C. and night temperatures ranged from ranged from 5° C. to 10° C. Plants were two years old when the detailed description was taken. In the following description, color references are made to The Royal Horticultural Society Colour Chart, 2015 Edition, except where general terms of ordinary dictionary significance are used.

Botanical classification: *Ilex glabra* 'SMNIGCM'.

Parentage:

*Female, or seed, parent*.—Unnamed proprietary selection of *Ilex glabra*, not patented.

*Male, or pollen, parent*.—Unknown proprietary selection of *Ilex glabra*, not patented.

Propagation:

*Type*.—By softwood cuttings.

*Time to initiate roots, summer*.—About 30 days at temperatures ranging from about 18° C. to 27° C.

*Time to produce a rooted young plant, summer*.—About five months at temperatures ranging from about 18° C. to 27° C.

*Root description*.—Medium in thickness, fibrous; typically brownish in color, actual color of the roots is dependent on substrate composition, water quality, fertilizer, substrate temperature and physiological age of roots.

*Rooting habit*.—Freely branching; dense.

Plant description:

*Plant and growth habit*.—Perennial evergreen shrub; compact and low and uniformly mounding plant habit; hemispherical and close to globose in overall plant shape; vigorous growth habit and moderate growth rate.

*Plant height*.—About 45 cm.

*Plant diameter, area of spread*.—About 80 cm.

*Lateral branch description*.—Branching habit: Freely branching habit; dense and bushy growth habit with about 20 primary lateral branches each with about six to eight secondary lateral branches developing per plant; dense and bushy plant habit. Length, primary lateral branches: About 35 cm. Length, secondary lateral branches: About 20 cm. Diameter: About 3 mm. Internode length: About 1 cm. Strength: Strong. Aspect: About 10° to 30° from vertical. Texture and luster: Smooth, glabrous; becoming woody with development; matte. Color, developing: Close to 146C. Color, developed: Close to 146B; when woody, close to N200B.

*Leaf description*.—Arrangement: Alternate, simple. Length: About 4 cm. Width: About 1 cm. Shape: Oblanceolate. Apex: Broadly acute. Base: Attenuate. Margin: Mostly entire; distally, two to four shallow serrations. Venation pattern: Pinnate. Texture and luster, upper surface: Smooth, glabrous; glossy. Texture and luster, lower surface: Smooth, glabrous; matte. Color: Developing and fully expanded leaves, upper surface: Close to 144A; venation, close to 144A. Developing and fully expanded leaves, lower surface: Close to 147B; venation, close to 147B. Petioles: Length: About 6 mm. Diameter: About 1 mm. Texture and luster, upper and lower surfaces: Smooth, glabrous; matte. Color, upper and lower surfaces: Close to 144B.

Flower description:

*Flower appearance and arrangement*.—Single terminal and axillary rotate flowers arranged in clusters; about 100 to 200 flower buds and flowers developing per plant; flowers face mostly outwardly; flowers pistillate and to date, stamen development has not been observed.

*Natural flowering season*.—Plants flower in May and June in Michigan.

*Flower longevity*.—Depending on temperature, individual flowers last about one week; flowers not persistent.

*Fragrance*.—None detected.

*Flower diameter*.—About 7 mm.

*Flower depth*.—About 3 mm.

*Flower buds*.—Length: About 2 mm. Diameter: About 2 mm. Shape: Orbicular. Texture and luster: Smooth, glabrous; matte. Color: Close to 146C.

*Petals*.—Quantity and arrangement: About five to seven in a single whorl; fused at the base. Length: About 2 mm. Width: About 1.5 mm. Shape: Oblong. Apex: Obtuse. Margin: Entire; not undulate. Texture and luster, upper and lower surfaces: Smooth, glabrous; silky; matte. Color: When opening, upper and lower surfaces: Close to 155A. Fully opened, upper and lower surfaces: Close to 155A; color does not change with subsequent development.

*Sepals*.—Quantity and arrangement: Five sepals arranged in a single whorl; sepals are minute, inconspicuous and difficult to measure due to their size; sepal length is less than 0.5 mm.

*Peduncles*.—Length: About 5 mm. Diameter: About 0.5 mm. Aspect: About 45° from lateral branch axis. Strength: Moderately strong. Texture and luster: Smooth, glabrous; matte. Color: Close to 146C.

*Reproductive organs*.—Androecium: flowers of the new *Ilex* are pistillate and do not form stamens. Pistils: Quantity per flower: One. Pistil length: About 2 cm. Style length: About 1.75 cm. Style color: Close to 144A. Stigma diameter: About 1 mm. Stigma shape: Flattened. Stigma color: Close to 144A. Ovary color: Close to 144A. Fruits: Quantity: About ten fruits are produced per lateral branch and about 100 fruits are produced per plant. Length: About 5 mm. Diameter: About 5 mm. Shape: Spherical. Texture and luster: Smooth, glabrous; glossy. Color: Close to 203B. Seeds: Quantity: About 1 to 3 seeds develop per fruit. Length: About 3 mm. Diameter: About 2 mm. Color: Close to N200C.

Garden performance: Plants of the new *Ilex* have been observed to have good garden performance and to tolerate wind, rain and temperatures ranging from −31° C. to 38° C.

Pathogen & pest resistance: To date, plants of the new *Ilex* have not been observed to be resistant to Holly Leaf Blight (*Phytophthora ilicis* or *Alternaria alternata*) and Holly Rust (*Pucciniales* sp.) pathogens. Plants of the new *Ilex* have not been observed to be resistant to pests and other pathogens common to *Ilex* plants.

It is claimed:

1. A new and distinct *Ilex* plant named 'SMNIGCM' as herein illustrated and described.

* * * * *